US008618332B2

United States Patent
Li Bassi et al.

(10) Patent No.: US 8,618,332 B2
(45) Date of Patent: Dec. 31, 2013

(54) PROCESS FOR THE PREPARATION OF CRYSTALLINE MIXTURES OF ALPHA-HYDROXYCARBONYL DERIVATIVES OF ALPHA-METHYLSTYRENE DIMERS

(75) Inventors: Giuseppe Li Bassi, Gavirate (IT); Gabriele Norcini, Comabbio (IT); Leonardo Federici, Buscate (IT)

(73) Assignee: Lamberti SpA, Albizzate (VA) (IT)

( * ) Notice: Subject to any disclaimer, the term of this patent is extended or adjusted under 35 U.S.C. 154(b) by 35 days.

(21) Appl. No.: 13/255,892

(22) PCT Filed: Mar. 10, 2010

(86) PCT No.: PCT/EP2010/053021
§ 371 (c)(1),
(2), (4) Date: Sep. 9, 2011

(87) PCT Pub. No.: WO2010/103035
PCT Pub. Date: Sep. 16, 2010

(65) Prior Publication Data
US 2012/0029238 A1    Feb. 2, 2012

(30) Foreign Application Priority Data

Mar. 11, 2009 (IT) .............................. VA2009A0018

(51) Int. Cl.
*C07C 45/61* (2006.01)
(52) U.S. Cl.
USPC .................. 568/327; 522/36; 522/85; 522/96
(58) Field of Classification Search
USPC .................................. 568/327; 522/36, 85, 96
See application file for complete search history.

(56) References Cited

U.S. PATENT DOCUMENTS 4,987,159 A * 1/1991 Li Bassi et al. ................. 522/36
6,995,290 B2 * 2/2006 Visconti et al. ............... 568/327

* cited by examiner

*Primary Examiner* — Sikarl Witherspoon
(74) *Attorney, Agent, or Firm* — Mossman, Kumar & Tyler, PC

(57) ABSTRACT

Process for the preparation of the powdery crystalline mixtures of alpha-hydroxycarbonyl derivatives of alpha-methylstyrene dinners comprising the use of a solvent having polarity from 0 to 0.1.

15 Claims, No Drawings

PROCESS FOR THE PREPARATION OF CRYSTALLINE MIXTURES OF ALPHA-HYDROXYCARBONYL DERIVATIVES OF ALPHA-METHYLSTYRENE DIMERS

The present invention relates to a process for the preparation of crystalline mixtures of alpha-hydroxycarbonyl derivatives of alpha-methylstyrene dimers. The use of oligomeric and bifunctional photoinitiators in the photopolymerization has several advantages in comparison to the use of monomeric and monofunctional photoinitiators, such as a lower migratability of the photoinitiator from the formulation and a reduced amount of volatile compounds derived from their photodecomposition. These characteristics are important for the industrial use because they reduce the risk of contamination of the finished product with unwanted compounds.

Among oligomeric photoinitiators the alpha-hydroxycarbonyl derivatives of oligomers of alpha-methylstyrene are known.

These photoinitiators are described, for instance, in U.S. Pat. No. 4,987,159.

They are mainly constituted by a mixture of dimer and trimer isomers. At room temperature the mixture is a very highly viscous product that cannot be easily used as such in industrial applications.

In the present text with the expression "mixture of alpha-hydroxycarbonyl derivatives of oligomers of alpha-methylstyrene" we refer to mixtures of compounds of Formula I, wherein n is a number equal or greater than 0:

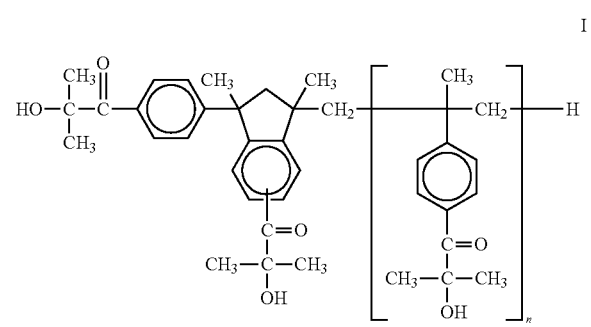

In the U.S. Pat. No. 4,987,159, the Applicant describes the preparation of a mixture of alpha-hydroxycarbonyl derivatives of oligomers of alpha-methylstyrene (mainly dimers and trimers), by: oligomerization and simultaneous cyclization of alpha-methylstyrene; subsequent introduction of carbonyl groups on the aromatic rings by reaction with isobutyryl chloride; chlorination of the alpha-position of the carbonyl; and final hydrolysis, to give the desired mixture.

The mixture of alpha-hydroxycarbonyl derivatives of oligomers of alpha-methylstyrene of U.S. Pat. No. 4,987,159 is a product with a pour point of from 40 to 50° C.

In the present text, this product is also indicated with the expression "high viscosity mixture".

International application WO 02/085832, filed by the same Applicant, describes a process for the preparation of solid mixtures of alpha-hydroxycarbonyl derivatives of oligomers of alpha-methylstyrene containing at least 90% of dimer isomers and wherein the more reactive dimer isomer prevails, starting from high viscosity mixtures containing at least 60% by weight of dimer isomers.

The process for the preparation of the solid mixtures of alpha-hydroxycarbonyl derivatives of oligomers of alpha-methylstyrene of WO 02/085832 consists in dissolving the high viscosity mixture in a specific amount of solvent having polarity between 0.1 and 0.7, precipitating and collecting the solid mixture. Unfortunately, solvents having polarity between 0.1 and 0.7 produce solid mixtures which are sticky and difficult to collect, especially when attempts are made to completely precipitate the dimers 5 and 6 from the high viscosity mixture of alpha-hydroxycarbonyl derivatives of oligomers of alpha-methylstyrene, to increase the yield of solid product.

International patent application, WO 2004/099111, filed by CIBA, describes an alternative procedure for the preparation of crystalline alpha-hydroxycarbonyl derivatives of dimers of alpha-methylstyrene; this preparation proceeds from pure 1,1,3-trimethyl-3-phenylindan having a low oligomers content and through a specific synthetic pathway comprising the use of isobutyryl chloride and chlorination with sulfuryl chloride or chlorine gas.

Italian patent application IT VA2006A000021 discloses a convenient process for the preparation of alpha-hydroxycarbonyl derivatives of oligomers of alpha-methylstyrene that does not include a chlorination step.

It has now been found that powdery crystalline mixtures of alpha-hydroxycarbonyl derivatives of alpha-methylstyrene dimers can be readily prepared in high yield and purity from mixtures of alpha-hydroxycarbonyl derivatives of oligomers of alpha-methylstyrene, that can be readily prepared as described in U.S. Pat. No. 4,987,159 or in IT VA2006A000021.

DETAILED DESCRIPTION

Accordingly, the invention is a process for the preparation of powdery crystalline mixtures of alpha-hydroxycarbonyl derivatives of alpha-methylstyrene dimers having high purity from mixtures of alpha-hydroxycarbonyl derivatives of oligomers of alpha-methylstyrene, in high yield. The powdery crystalline mixtures obtained from the process of the present invention comprise more than 95% of alpha-hydroxycarbonyl derivatives of alpha-methylstyrene dimers, the ratio of the dimer 5 to dimer 6 being from 1.5 to 7.0 (HPLC purity measured as specified in the analytical method here below reported).

The expression "dimer isomer 5" or "dimer 5" refers to the product of Formula II.

Formula II:

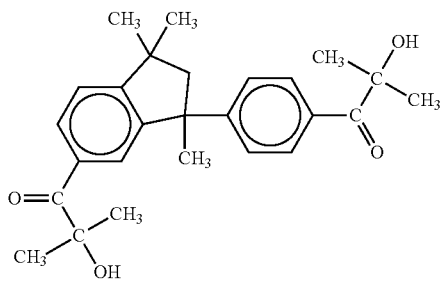

dimer isomer 5

The expression "dimer isomer 6" or "dimer 6" refers to the product of Formula III.

Formula III:

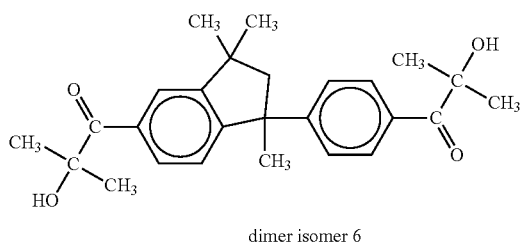

dimer isomer 6

The expression "alpha-hydroxycarbonyl derivatives of dimers of alpha-methylstyrene" refers to dimers 5 and 6.

The mixtures of alpha-hydroxycarbonyl derivatives of oligomers of alpha-methylstyrene useful as the starting product may be prepared as reported in U.S. Pat. No. 4,987,159 or in IT VA2006A000021.

The process for the preparation of the powdery crystalline mixtures of alpha-hydroxycarbonyl derivatives of alpha-methylstyrene dimers comprises the following step: a) dissolving a mixture of alpha-hydroxycarbonyl derivatives of oligomers of alpha-methylstyrene in a solvent with a polarity between 0.1 and 0.7, preferably between 0.25 and 0.6, with a ratio solvent/mixture of alpha-hydroxycarbonyl derivatives of oligomers of alpha-methylstyrene between 0.2 and 4, preferably between 0.4 and 2.5; b) keeping the mixture at temperature below 40° C. for from 10 to 120 hours; c) collecting by filtration the thus obtained solid precipitate and washing it with at least 1 parts by weight of a solvent having polarity from 0 to 0.1; d) removing the solvent residues by conventional methods.

The mixture of alpha-hydroxycarbonyl derivatives of oligomers of alpha-methylstyrene of step a) generally contain at least 60% by weight of the dimer isomers 5 and 6.

The polarity of the solvent ($\square$°) corresponds to the absorption energy measured on $Al_2O_3$.

Step c) is preferably performed at temperature from 20 to 100° C., under stirring.

Example of suitable solvents of step c) are $C_5$-$C_8$ aliphatic hydrocarbons having boiling point below 140° C., such as n-hexane, petroleum ether, n-pentane, cyclopentane, cyclohexane, isooctane, n-octane, n-heptane and mixture thereof, n-hexane being the preferred solvent.

The procedure of the invention has the great advantage that almost all of the dimers 5 and 6 can be recovered in powdery crystalline form having a purity of at least 95% by weight, preferably of 97% or more which is highly reactive as photoinitiator.

Another relevant advantage is that the procedure does not involve the use and the consequent control of gaseous reagents, such as chlorine or other reagents that can produce sulfurized gaseous by-products which are environmentally noxious.

The thus isolated powdery crystalline mixture of dimers has a much better flowability than the solid mixture obtained according to WO 02/085832; moreover, the crystalline mixture is devoid of monofunctional alpha-hydroxycarbonyl derivatives impurities (such as 2-hydroxy-2-methyl-1-phenyl-1-propanone), which are usual by-products of the synthesis (generated by the acid catalyzed cleavage—dearylation—of phenylindane groups). 2-hydroxy-2-methyl-1-phenyl-1-propanone is a migratable substance; therefore, for many uses in the photocuring industry it is highly desirable to obtain the crystalline mixture of alpha-hydroxycarbonyl derivatives of dimers of alpha-methylstyrene with the lowest possible content of 2-hydroxy-2-methyl-1-phenyl-1-propanone.

The powdery crystalline mixtures of alpha-hydroxycarbonyl derivatives of dimers of alpha-methylstyrene obtained from the process of the present invention contains less than 0.1% of 2-hydroxy-2-methyl-1-phenyl-1-propanone, the content of 2-hydroxy-2-methyl-1-phenyl-1-propanone being determined as the % of chromatographic area obtained from HPLC analytical method using a UV 265 nm detector.

When the process of WO/085832 and the process of the present invention are used in combination a particularly advantageous product is obtained, having purity of 95% or more in dimers 5 and 6, excellent flowability and the high reactivity which is typical of dimers 5 and 6 mixtures in which the ratio of the dimer isomer 5 to the dimer isomer 6 is between 2.5 and 7.

In another advantageous embodiment the crystallization step b) is prolonged until 60% or more of the dimers 5 and 6 is precipitated and washed as described in step c), thus obtaining a higher yield of a product having purity of at least 95% in dimers, excellent flowability and high reactivity, which is typical of dimers 5 and 6 mixtures in pure form.

In the latter embodiment the ratio of the dimer isomer 5 to the dimer isomer 6 is below 2.5, but the reactivity of the crystalline mixture is higher than that of the starting mixtures of alpha-hydroxycarbonyl derivatives of oligomers of alpha-methylstyrene due to the enhanced purity.

The powdery crystalline mixtures of alpha-hydroxycarbonyl derivatives of alpha-methylstyrene dimers obtained according to the procedure of the present invention are used as photoinitiators in the energy curing technology, in particular for the photocuring of formulations containing unsaturated compounds or mixtures of unsaturated compounds of the acrylic and/or methacrylic type.

Among the preferred uses of the crystalline mixtures of the invention we cite their use as photoinitiators in low-yellowing paints and varnishes, food packaging coatings, adhesives, graphic arts, industrial coatings, optical fibers coatings, photocuring compositions for printing plates.

In the following examples the measurement of the content of the dimer isomers, of the ratio between the two dimer isomers 5 and 6 and of 2-hydroxy-2-methyl-1-phenyl-1-propanone reported in examples was carried out by HPLC (high performance liquid chromatography). The chromatographic conditions were: nova-pack column PR18-15 cm×3.9 mm-4 $\square$m and pre-column; eluent A=20% methanol in water, eluent B=methanol; gradient from 100% A to 100% B in 30 min, 100% B 10 min, 100% A 20 min; flow rate 0.8 ml/min, detector 265 nm.

EXAMPLES

Example 1

Comparative

The precipitation of the solid mixture is carried out with toluene as solvent ($\square$°0.29) using a high viscosity mixture with a dimers content of 85.1% and a ratio between the dimer isomers 5 and 6 of 1.93. This high viscosity mixture was obtained as reported in Example 10 of the U.S. Pat. No. 4,987,159.

14 kg of toluene are transferred into a heated reactor, set at a temperature of 120° C., and 28 kg of Mixture 1 are added under stirring. After complete dissolution the temperature is set at 20° C. and a small portion of a previously precipitated product is added.

The precipitation mixture is left at 20° C. under stirring for 48 hours. The precipitate is filtered by suction and washed twice with toluene. The cake is dried under vacuum (200 mmHg) and stirring at 25° C.; after 16 hours the residual toluene content is less than 0.5%.

The amount of dried precipitate, which is in the form of an irregular powder, containing coarse agglomerates (from 1 to 30 mm) is 11.8 kg (yield 41.3%); the content of the dimer isomers is 96.8% and the ratio of the dimer isomers 5 and 6 is 2.93.

% (chromatographic area) of 2-hydroxy-2-methyl-1-phenyl-1-propanone impurity=0.37%

Example 2

Comparative 200 g of high viscosity mixture with a dimers content of 90.4% and a ratio between the dimer isomer 5 and 6 of 2.09, were dissolved under stirring in 200 g of toluene at reflux. After complete dissolution the mixture was cooled at room temperature (18° C.) and 2 g of previously precipitated product were added. The mixture was maintained under stirring at the same temperature for 72 hrs. After 48 hrs and after 72 hrs a sample was collected to evaluate the yield of crystallization by filtration; the composition of the solid was also evaluated by HPLC. The results are reported in the Table 1.

TABLE 1

| t (hours) | yield % | purity % | Impurity[1] % | Dimers 5/6 ratio |
|---|---|---|---|---|
| 48 | 51.6 | 96.81 | 0.,17 | 3.07 |
| 72 | 67.9 | 96.58 | 0.21 | 2.13 |

[1]2-hydroxy-2-methyl-1-phenyl-1-propanone

Example 3

118 g of high viscosity mixture with a dimers content of 87.2% and a ratio between the dimer isomer 5 and 6 of 1.98 g was dissolved under stirring in 118 g of toluene at reflux. After complete dissolution the mixture was cooled at room temperature (18° C.) and 2 g of previously crystallized product were added. The mixture was maintained under stirring at the same temperature for 72 hrs and the mother liquor was filtered off by suction. The solid was suspended in 150 g of n-hexane and stirred at reflux for 1 hr, then after cooling the solid was collected by filtration. The cake was dried under vacuum and stirring; after 12 hours the residual solvent content was less than 0.5%. 77.5 g of product were was collected as a white, free flowable powder (65.7%), mp 99°-100° C., particle size: 20-25%>16 mesh, 25-35% 16-35 mesh, 5-10% 35-45 mesh, 30-50%<45 mesh; the HPLC and other analysis data are reported in Table 2.

TABLE 2

| sample | purity % | Impurity[1] % | Dimers 5/6 ratio |
|---|---|---|---|
| before washing with n-hexane | 95.22 | 0.39 | 2.16 |
| after washing with n-hexane | 97.34 | 0.09 | 2.37 |

[1]2-hydroxy-2-methyl-1-phenyl-1-propanone

The invention claimed is:

1. A process for preparation of powdery crystalline mixtures of alphahydroxycarbonyl derivatives of alpha-methylstyrene dimers comprising:
   dissolving a mixture of alpha-hydroxycarbonyl derivatives of oligomers of alpha-methylstyrene in a solvent having a polarity of from about 0.1 to about 0.7, at a ratio of solvent to mixture of alphahydroxycarbonyl derivatives of oligomers of alpha-methylstyrene of from about 0.2 to about 4;
   maintaining the mixture of alpha-hydroxycarbonyl derivatives of oligomers of alpha -methylstyrene in the solvent at a temperature no higher than about 40° C. for from about 10 to about 120 hours;
   collecting by filtration a solid precipitate and washing it with at least 1 part by weight of a solvent having polarity from about 0 to about 0.1; and
   removing the solvent.

2. The process of claim 1 wherein the mixture of alpha-hydroxycarbonyl derivatives of oligomers of alpha-methylstyrene comprises at least 60% by weight of dimer isomers 5 and 6.

3. The Process of claim 2 wherein the collecting by filtration of the solid precipitate and washing it with at least 1 part by weight of a solvent having polarity from about 0 to about 0.1 is performed at a temperature of from about 20 to about 100° C., under stirring.

4. The Process of claim 2 wherein the solvent used to maintain the mixture of alpha-hydroxycarbonyl derivatives of oligomers of alpha-methylstyrene at a temperature no higher than about 40° C. for from about 10 to about 120 hours is a $C_5$-$C_8$ aliphatic hydrocarbon having boiling point below 140° C.

5. The Process of claim 3 wherein the solvent used to maintain the mixture of alpha-hydroxycarbonyl derivatives of oligomers of alpha-methylstyrene at a temperature no higher than about 40° C. for from about 10 to about 120 hours is a $C_5$-$C_8$ aliphatic hydrocarbon having boiling point below 140° C.

6. The Process of claim 4 wherein the solvent used to maintain the mixture of alpha-hydroxycarbonyl derivatives of oligomers of alpha-methylstyrene at a temperature no higher than about 40° C. for from about 10 to about 120 hours is selected from the group consisting of n-hexane, petroleum ether, n-pentane, cyclopentane, cyclohexane, isooctane, n-octane, n-heptane, and mixture thereof.

7. The Process of claim 5 wherein the solvent used to maintain the mixture of alpha-hydroxycarbonyl derivatives of oligomers of alpha-methylstyrene at a temperature no higher than about 40° C. for from about 10 to about 120 hours is selected from the group consisting of n-hexane, petroleum ether, n-pentane, cyclopentane, cyclohexane, isooctane, n-octane, n-heptane, and mixture thereof.

8. The Process of claim 7 wherein the solvent used to maintain the mixture of alpha-hydroxycarbonyl derivatives of oligomers of alpha-methylstyrene at a temperature no higher than about 40° C. for from about 10 to about 120 hours is n-hexane.

9. A composition comprising crystalline mixtures of alpha-hydroxycarbonyl derivatives of dimers of alpha-methylstyrene having purity higher than 95% by weight and containing less than 0.1% of 2-hydroxy-2-methyl-l-phenyl-lpropanone.

10. The composition of claim 9 wherein the content of 2-hydroxy-2-methyl-l-phenyl-1-propanone is determined as the % of chromatographic area obtained from HPLC analytical method using a UV 265 nm detector.

11. The composition of claim 10 wherein the crystalline mixtures of alpha-hydroxycarbonyl derivatives of dimers of alpha-methylstyrene have a purity higher than 97% by weight.

12. The composition of claim 9 wherein the composition is a photoinitiator.

13. The composition of claim 11 wherein the composition is a photoinitiator.

14. The composition of claim 9 wherein the composition is a photoinitiator useful in the production of food packaging coatings, low-yellowing paints and varnishes, adhesives, graphic arts, industrial coatings, optical fibers coatings; and for photocuring compositions for printing plates.

15. The composition of claim 11 wherein the composition is a photoinitiator useful in the production of food packaging coatings, low-yellowing paints and varnishes, adhesives, graphic arts, industrial coatings, optical fibers coatings; and for photocuring compositions for printing plates.

* * * * *